(12) United States Patent
Miller

(10) Patent No.: US 9,554,916 B2
(45) Date of Patent: Jan. 31, 2017

(54) APPARATUS AND METHOD FOR REPLACEMENT OF A METATARSOPHALANGEAL JOINT WITH INTERPHALANGEAL FUSION

(71) Applicant: Sarah Miller, Highland Park, IL (US)

(72) Inventor: Sarah Miller, Highland Park, IL (US)

(*) Notice: Subject to any disclaimer, the term of this patent is extended or adjusted under 35 U.S.C. 154(b) by 0 days.

(21) Appl. No.: 14/723,879

(22) Filed: May 28, 2015

(65) Prior Publication Data

US 2015/0351921 A1   Dec. 10, 2015

Related U.S. Application Data

(60) Provisional application No. 62/007,527, filed on Jun. 4, 2014.

(51) Int. Cl.
*A61F 2/42* (2006.01)
*A61F 2/30* (2006.01)

(52) U.S. Cl.
CPC .... *A61F 2/4225* (2013.01); *A61F 2002/30205* (2013.01); *A61F 2002/30405* (2013.01); *A61F 2002/30622* (2013.01); *A61F 2002/4235* (2013.01)

(58) Field of Classification Search
CPC ... A61F 2/4241; A61F 2002/4243–2002/4258; A61F 2/4261; A61F 2002/4264–2002/4297; A61F 2/4225; A61F 2002/4228–2002/4238; A61F 2/40; A61F 2/4606; A61F 2002/3822; A61F 2002/3831; A61F 2/385; A61F 2/3854

USPC ............... 623/21.19, 21.11, 21.14, 21.18
See application file for complete search history.

(56) References Cited

U.S. PATENT DOCUMENTS

| | | | | |
|---|---|---|---|---|
| 4,156,296 A | * | 5/1979 | Johnson | A61F 2/4225 623/21.19 |
| 5,326,366 A | * | 7/1994 | Pascarella | A61F 2/4225 623/21.19 |
| 5,405,401 A | | 4/1995 | Lippincott, III et al. | |
| 5,458,648 A | * | 10/1995 | Berman | A61F 2/4225 623/21.19 |
| 5,480,447 A | | 1/1996 | Skiba | |
| 5,667,510 A | * | 9/1997 | Combs | A61B 17/15 606/286 |
| 5,683,466 A | * | 11/1997 | Vitale | A61F 2/30756 623/21.15 |
| 5,938,699 A | * | 8/1999 | Campbell | A61F 2/4261 623/21.13 |
| 6,007,580 A | | 12/1999 | Lehto et al. | |

(Continued)

*Primary Examiner* — Alvin Stewart
(74) *Attorney, Agent, or Firm* — Young Basile Hanlon & MacFarlane P.C.

(57) ABSTRACT

An apparatus and method for partial replacement of a metatarsophalangeal joint defined by a proximal face of a phalanx and a distal face of a metatarsal. The apparatus and method include a joint surface element and an elongated fusing element. The elongated fusing element has an end configured for tool engagement. The joint surface element has a generally concave surface configured to serve as the proximal face of the phalanx and a socket configured to engage the end of the elongated fusing element. The elongated fusing element fuses an interphalangeal joint when the apparatus is surgically implanted to prevent the deterioration of the interphalangeal joint.

19 Claims, 3 Drawing Sheets

(56) References Cited

U.S. PATENT DOCUMENTS

| | | | | |
|---|---|---|---|---|
| 6,099,571 A * | 8/2000 | Knapp | A61F 2/4225 | 623/18.11 |
| 6,409,768 B1 * | 6/2002 | Tepic | A61B 17/725 | 606/64 |
| 6,610,099 B1 * | 8/2003 | Albrektsson | A61B 17/8635 | 623/23.11 |
| 6,663,669 B1 * | 12/2003 | Reiley | A61B 17/15 | 623/21.11 |
| 7,291,175 B1 * | 11/2007 | Gordon | A61F 2/4225 | 606/98 |
| 7,837,738 B2 * | 11/2010 | Reigstad | A61B 17/1686 | 623/21.11 |
| 7,909,880 B1 * | 3/2011 | Grant | A61F 2/4225 | 623/21.19 |
| 8,292,966 B2 * | 10/2012 | Morton | A61B 17/15 | 623/21.19 |
| 8,597,337 B2 | 12/2013 | Champagne | | |
| 8,652,211 B1 * | 2/2014 | Jerry, Jr. | A61F 2/4225 | 623/21.19 |
| 9,132,018 B1 * | 9/2015 | Hajianpour | A61F 2/4202 | |
| 2002/0111690 A1 * | 8/2002 | Hyde | A61B 17/1604 | 623/18.12 |
| 2003/0045881 A1 | 3/2003 | Barouk et al. | | |
| 2003/0083662 A1 * | 5/2003 | Middleton | A61B 17/0401 | 606/323 |
| 2004/0230313 A1 * | 11/2004 | Saunders | A61F 2/4225 | 623/21.19 |
| 2005/0049710 A1 * | 3/2005 | O'Driscoll | A61F 2/3804 | 623/20.11 |
| 2005/0216090 A1 * | 9/2005 | O'Driscoll | A61F 2/3804 | 623/20.32 |
| 2005/0229433 A1 * | 10/2005 | Cachia | A61B 17/562 | 36/44 |
| 2006/0009853 A1 * | 1/2006 | Justin | A61B 17/1659 | 623/20.3 |
| 2006/0052725 A1 * | 3/2006 | Santilli | A61F 2/3804 | 600/587 |
| 2006/0074492 A1 * | 4/2006 | Frey | A61F 2/4225 | 623/21.15 |
| 2006/0100715 A1 * | 5/2006 | De Villiers | A61F 2/4225 | 623/23.4 |
| 2006/0129153 A1 * | 6/2006 | Klaue | A61B 17/68 | 606/916 |
| 2006/0247787 A1 * | 11/2006 | Rydell | A61B 17/562 | 623/21.11 |
| 2006/0264951 A1 * | 11/2006 | Nelson | A61B 17/7208 | 606/916 |
| 2006/0276905 A1 * | 12/2006 | Calamel | A61F 2/34 | 623/22.28 |
| 2008/0195217 A1 * | 8/2008 | Scheker | A61F 2/3804 | 623/20.11 |
| 2008/0195233 A1 * | 8/2008 | Ferrari | A61F 2/4202 | 623/47 |
| 2008/0221697 A1 | 9/2008 | Graser | | |
| 2008/0269908 A1 * | 10/2008 | Warburton | A61B 17/15 | 623/21.15 |
| 2009/0254189 A1 * | 10/2009 | Scheker | A61F 2/4261 | 623/21.11 |
| 2009/0276052 A1 * | 11/2009 | Regala | A61F 2/30 | 623/18.11 |
| 2010/0057216 A1 * | 3/2010 | Gannoe | A61F 2/4202 | 623/21.18 |
| 2010/0106202 A1 * | 4/2010 | Gannoe | A61B 17/1659 | 606/86 R |
| 2010/0121390 A1 * | 5/2010 | Kleinman | A61B 17/15 | 606/86 R |
| 2010/0130978 A1 * | 5/2010 | Orbay | A61B 17/7283 | 606/62 |
| 2010/0211120 A1 * | 8/2010 | Bonutti | A61B 17/0401 | 606/86 R |
| 2011/0004255 A1 * | 1/2011 | Weiner | A61B 17/1682 | 606/301 |
| 2011/0077744 A1 * | 3/2011 | Imbriglia | A61F 2/4261 | 623/21.12 |
| 2011/0082561 A1 * | 4/2011 | Forrester | A61F 2/4225 | 623/21.19 |
| 2011/0093085 A1 * | 4/2011 | Morton | A61B 17/15 | 623/21.19 |
| 2011/0118739 A1 * | 5/2011 | Tyber | A61B 17/1717 | 606/62 |
| 2011/0118792 A1 * | 5/2011 | Orsak | A61B 17/1615 | 606/301 |
| 2011/0166608 A1 * | 7/2011 | Duggal | A61B 17/683 | 606/320 |
| 2011/0172781 A1 * | 7/2011 | Katrana | A61F 2/3804 | 623/20.11 |
| 2011/0257755 A1 * | 10/2011 | Bellemere | A61F 2/4241 | 623/21.15 |
| 2011/0282397 A1 * | 11/2011 | Richter | A61B 17/1717 | 606/304 |
| 2012/0010719 A1 * | 1/2012 | Reiley | A61B 17/72 | 623/21.18 |
| 2012/0136453 A1 * | 5/2012 | Scheker | A61F 2/4261 | 623/21.12 |
| 2012/0197254 A1 * | 8/2012 | Wolfe | A61B 17/1717 | 606/62 |
| 2012/0245701 A1 * | 9/2012 | Zak | A61F 2/4202 | 623/21.18 |
| 2012/0259419 A1 * | 10/2012 | Brown | A61F 2/4225 | 623/21.19 |
| 2013/0046387 A1 * | 2/2013 | Goswami | A61F 2/4225 | 623/21.19 |
| 2013/0197655 A1 * | 8/2013 | Scheker | A61F 2/4241 | 623/21.16 |
| 2013/0218286 A1 * | 8/2013 | Stahl Wernersson | A61F 2/4225 | 623/21.15 |
| 2014/0025124 A1 * | 1/2014 | Champagne | A61B 17/863 | 606/308 |
| 2014/0107712 A1 * | 4/2014 | Fallin | A61F 2/4241 | 606/308 |
| 2014/0142575 A1 * | 5/2014 | Biedermann | A61B 17/846 | 606/62 |
| 2014/0214095 A1 * | 7/2014 | Rosenwasser | A61B 17/66 | 606/301 |
| 2015/0032168 A1 * | 1/2015 | Orsak | A61F 2/4202 | 606/304 |
| 2015/0057665 A1 * | 2/2015 | Neal | A61B 17/15 | 606/87 |
| 2015/0094724 A1 * | 4/2015 | Champagne | A61F 2/4606 | 606/79 |
| 2015/0142066 A1 * | 5/2015 | Shemwell | A61B 17/8888 | 606/301 |
| 2015/0250602 A1 * | 9/2015 | Sikora | A61F 2/40 | 623/19.12 |
| 2015/0351815 A1 * | 12/2015 | Wales | A61F 2/08 | 606/323 |

* cited by examiner

APPARATUS AND METHOD FOR REPLACEMENT OF A METATARSOPHALANGEAL JOINT WITH INTERPHALANGEAL FUSION

PRIORITY

This application claims the benefit of U.S. Provisional Application No. 62/007,527 filed on Jun. 4, 2014, which is incorporated by reference herein in its entirety.

TECHNICAL FIELD

The invention relates generally to artificial joint implants, and more particularly, an apparatus and method that provide for the partial replacement of a metatarsophalangeal joint.

BACKGROUND

Prosthetic implant devices are well known for the purpose of completely or partially replacing existing skeletal joints in the human body. In the human foot, the metatarsophalangeal joint between the first metatarsal and the first phalanx, in what is commonly known as the hallux or great toe is the site of frequent occurrences of arthritic deterioration. As a result, much attention has been directed to full or partial replacement of the joint.

One technique known for partial replacement of the joint uses silicone based materials attached to the phalanx. When such material is in contact with the metatarsal head, however, these types of implants eventually break down, reducing their effectiveness and potentially damaging surrounding tissues. Likewise, attempts at full joint replacement using silicone material have produced results which are less than desirable.

Metal implant devices, typically of titanium, have been adopted as preferable substitutions for flexible silicone materials. Joint replacement may be full or partial (hemi). Where the metatarsal head remains intact, manageable results have been achieved by providing a metal implant device fixed to the phalanx head of the joint. It is generally not acceptable to replace both sides of the joint with metal implants, a procedure which frequently results in either joint discomfort or progressive dislocation of the joint, or both.

Hemi joint replacement is the preferred surgical procedure in cases where the metatarsophalangeal joint has deteriorated, while the metatarsal head remains intact. This procedure is generally indicated where the patient experiences painful arthritis or hallux valgus. A typical example of a hemi-implant for replacing a phalanx in the hallux is disclosed in U.S. Pat. No. 5,326,366 issued to Pascarella et al., entitled "Biomechanical Great Toe Implant".

Other joint replacement techniques involve full replacement of the joint, for example, as taught in U.S. Pat. No. 5,458,648 to Berman et al.; U.S. Pat. No. 5,314,486 issued to Zang et al.; and U.S. Pat. No. 6,699,292 issued to Ogilvie et al.

A known difficulty with using hemi implants in the metatarsophalangeal joint, however, is that hemi implants may cause deterioration of the nearby interphalangeal joint. For this reason, many surgeons will not use a hemi implant to partially replace the metatarsophalangeal joint.

A further solution to the problem, particularly useful in arthritic joints, is fusion of the distal phalanx and proximal phalanx, in conjunction with a hemi implant. By fusing the distal and proximal phalanxes as taught herein, a solid lever arm is created, thereby improving articulation between the first metatarsophalangeal joint and the proximal phalanx.

SUMMARY

The invention is an apparatus and method for partial replacement of a metatarsophalangeal joint defined by a proximal face of a phalanx and a distal face of a metatarsal. The apparatus and method include a joint surface element and an elongated fusing element. The elongated fusing element has an end configured for engagement with the joint surface element. The joint surface element has a generally concave surface configured to serve as the proximal face of the phalanx and a socket configured to engage the end of the elongated fusing element. The elongated fusing element fuses the interphalangeal joint when the apparatus is surgically implanted to prevent the deterioration of the interphalangeal joint.

BRIEF DESCRIPTION OF THE DRAWINGS

The various features, advantages, and other uses of the present apparatus will become more apparent by referring to the following detailed description and drawings, in which.

DETAILED DESCRIPTION

The present invention provides improved and beneficial characteristics in a device which fuses the distal and proximal phalanx while providing a partial joint replacement for the metatarsophalangeal joint, thereby improving patient mobility. The method of the present invention facilitates surgical placement of the prosthesis.

Figure 1:
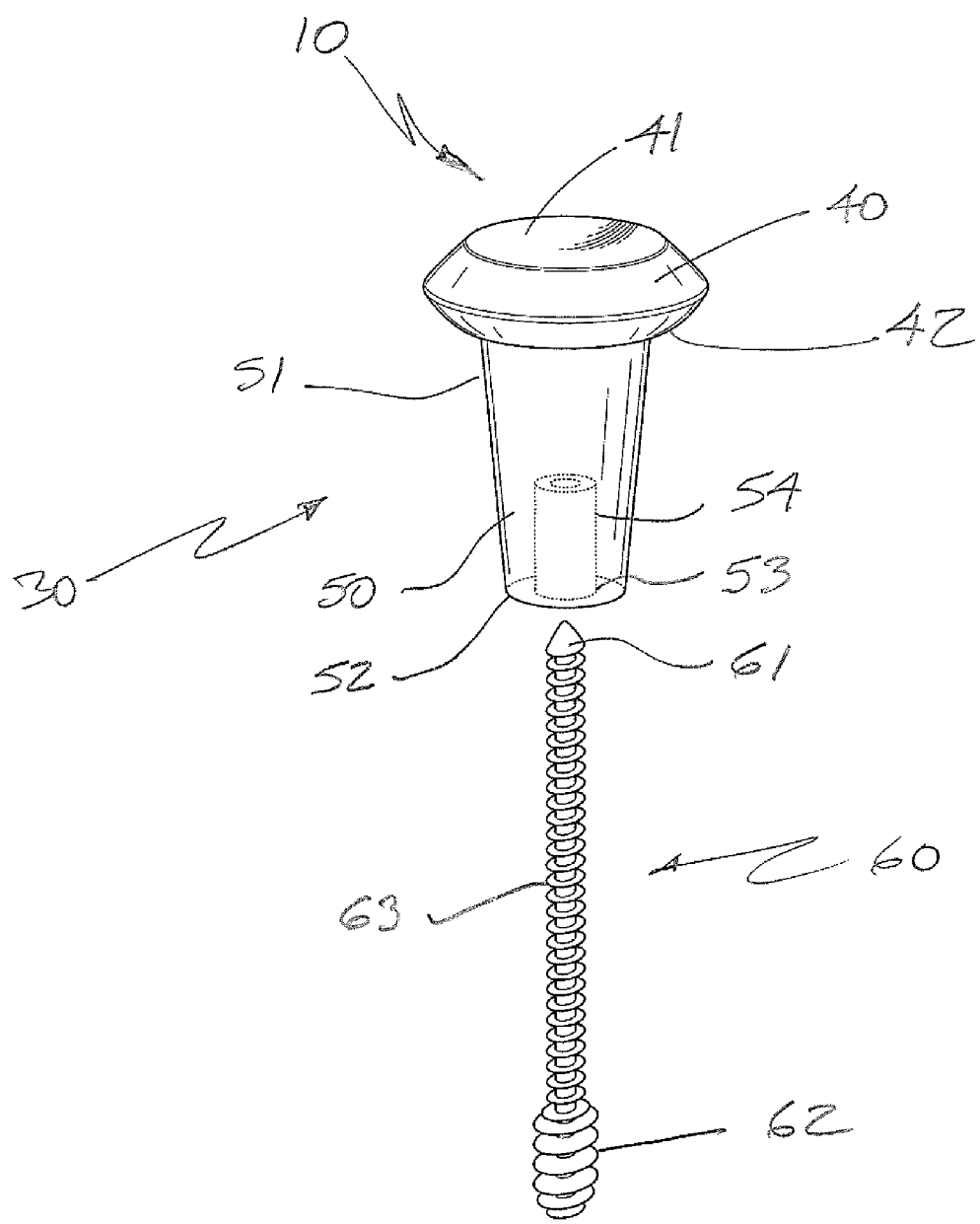
FIG. 1 is a side plan view of an apparatus that includes a hemi implant and a headless compression screw.
Figure 2:
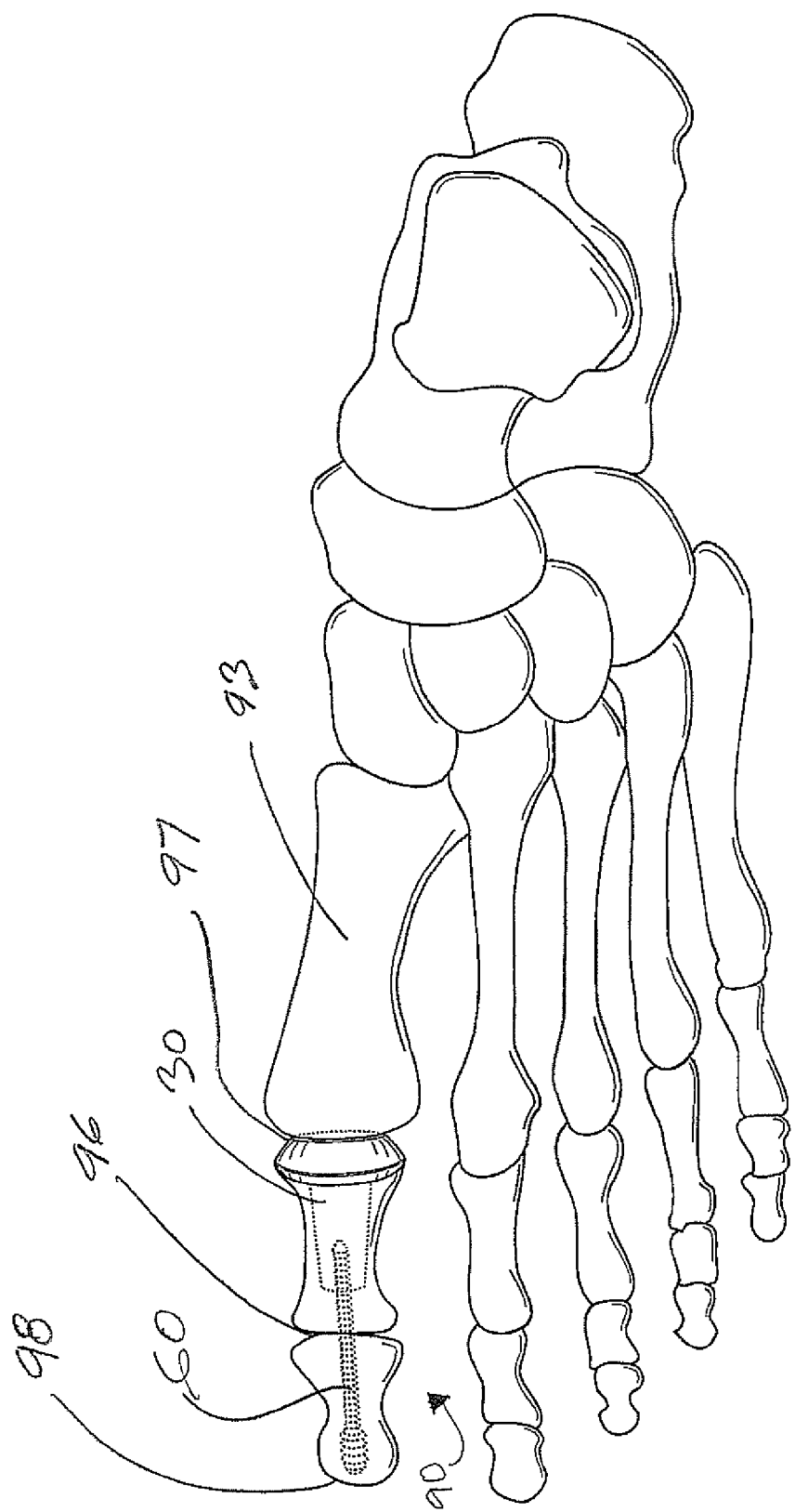
FIG. 2 is a top (dorsal) view of the skeletal structure of a human foot showing the apparatus implanted in a first metatarsophalangeal joint.
Figure 3:
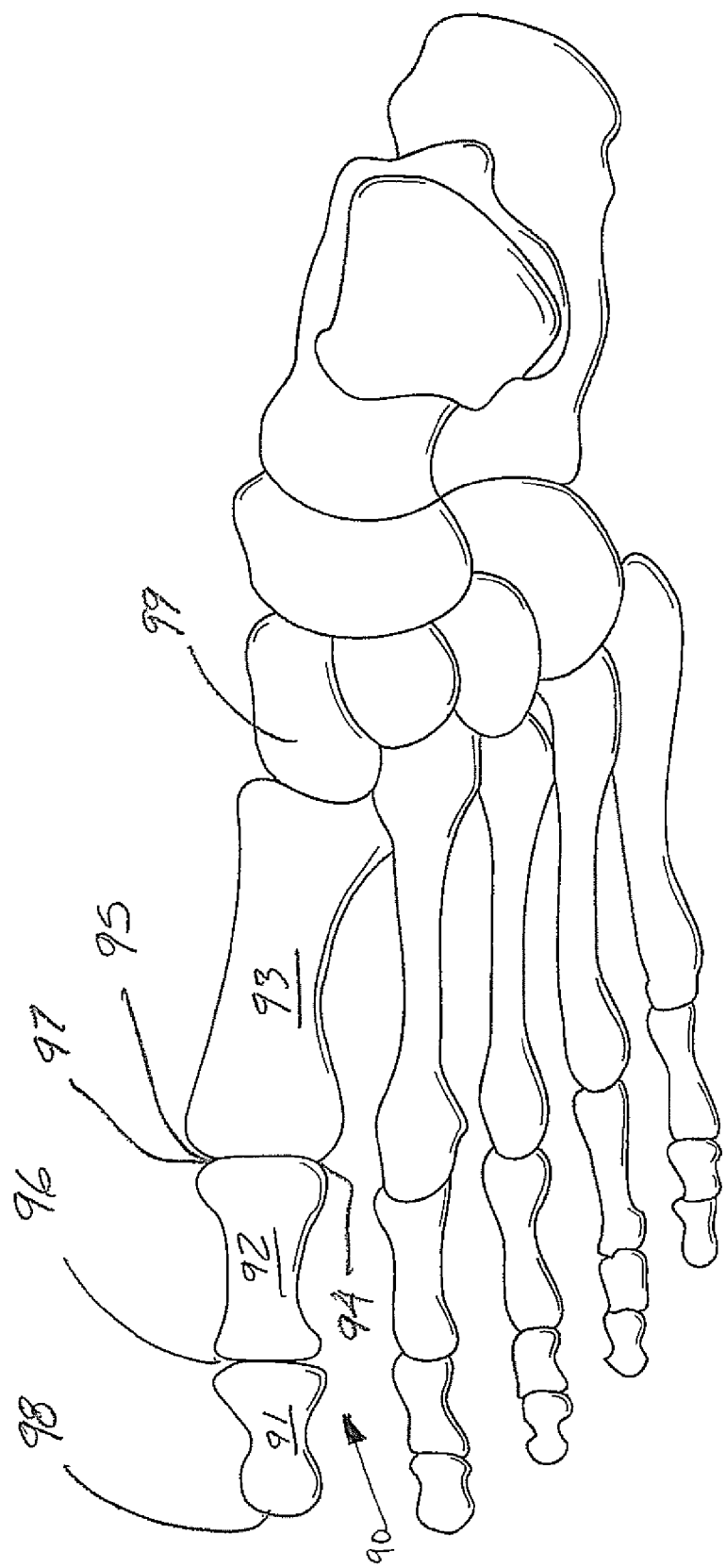
FIG. 3 is a top (dorsal) view of the skeletal structure of a human foot.

As depicted in FIGS. 1-3, the disclosure is directed to an apparatus 10 and associated surgical procedure that prevent the deterioration of an interphalangeal joint 96 by fusing the interphalangeal joint 96 when the metatarsophalangeal joint 97 is partially replaced. This disclosure describes the apparatus 10 and method as it relates to a hallux 90. However, it is anticipated that the apparatus 10 and method could be used on other joints.

The structure and intricacies of the human foot, and more specifically the hallux 90, are well known to those skilled in the art. The following description explains the skeletal structures that are relevant to the understanding of the apparatus 10 and method. As shown in FIG. 3, the hallux 90 includes a distal phalanx 91 and a proximal phalanx 92, which are joined by the interphalangeal joint 96 having an articular surface (not shown). The proximal face of the metatarsal 93 joins the medial cuneiform bone 99. The proximal face 94 of the proximal phalanx 92 is joined to the distal face 95 of the metatarsal 93 by the metatarsophalangeal joint 97. The apparatus of the present invention replaces the proximal face 94 of the proximal phalanx 92 and fuses the interphalangeal joint 96.

As shown in FIGS. 1 and 2, the apparatus 10 is comprised of two components: a joint surface element 30 and an elongated fusing element 60. The joint surface element 30 has a head portion 40 and a stem portion 50. The joint surface element 30 is preferably metallic, e.g., titanium. The head portion 40 may be substantially circular and has an upper surface 41 and a base 42. The upper surface 41 is spaced a longitudinal distance from the base 42. The upper surface 41 is generally concave, having geometry complimentary to the distal face 95 of metatarsal 93. In the preferred embodiment, upper surface 41 further comprises a smooth polished cobalt chromium surface providing low friction and high wear resistance. The head portion 40 is connected to the stem portion 50 at the base 42. The upper surface 41 is configured to serve as the proximal face 94 of the proximal phalanx 92, such as being generally concave and presenting a smooth polished surface. The size of the upper surface 41 is selected to be substantially the size of the proximal face 94 of the proximal phalanx 92 into which the joint surface element 30 will be implanted.

The stem portion 50 of joint surface element 30 is generally frustoconical and has a first end 51, a second end 52, and a socket 53. The stem portion 50 is tapered from the first end 51 to the second end 52, such that the second end 52 is smaller than the first end 51. The stem portion 50 is connected to the head portion 40 at the first end 51. The joint surface element 30, including the head portion 40 and the stem portion 50, is formed as a unit, such that the head portion 40 and the stem portion 50 are monolithic. The first end 51 of stem portion 50 is spaced a longitudinal distance from the second end 52. The socket 53 is a substantially hollow cylindrical cavity open on at least the second end 52 and centrally located inside the stem portion 50. The socket 53 is configured to engage an insert 54 and the elongated fusing element 60, for example, with complimentary threads. Preferably, socket 53 is provided with internal grooves, threads, or other engagement surfaces. The insert 54 is inserted into socket 53. The insert 54 is substantially tubular and formed so that its outer circumference engages and is secured to the wall of socket 53. The insert 54 may be, for example, threaded on its outer circumference to engage complimentary threads formed in socket 53. The insert 54 may also be secured to socket 53 utilizing adhesives or may be implanted into socket 53 using other well-known techniques to effectively fuse the insert to socket 53. By using elastomeric materials for the insert 54, the fusing element within described is effectively locked in rotational relationship with joint surface element 30.

The second major component of the apparatus 10 is elongated fusing element 60. As shown in FIG. 1, the elongated fusing element 60 is a slender, elongate member having surface features such as threads that are configured to engage bones, such as the distal phalanx 91 and the proximal phalanx 92 to restrain movement of the bones with respect to the elongated fusing element 60. The elongated fusing element 60 may be made of any suitable material, such as metal. An example of a suitable elongated fusing element 60 is a headless compression screw.

The elongated fusing element 60 has a first end 61, a second end 62, and a body portion 63. The first end 61 is spaced a longitudinal distance from the second end 62, and the body portion 63 is located between the first end 61 and the second end 62. The body portion 63 may be threaded. The first end 61 is configured to engage the socket 53 and the insert 54 of the joint surface element 30. The longitudinal distance between the first end 61 and the second end 62 must be sufficient to ensure that the elongated fusing element 60 extends through the interphalangeal joint 96, but short enough that it does not project through the distal end 98 of the hallux 90, when the first end 61 of the elongated fusing element 60 is engaged with the socket 53 of the joint surface element 30. Elongated fusing element 60 is configured with and incorporates a tool-engageable head. The fusing element may be in the form of a headless compression screw, of the type provided with self-drilling and self-tapping threads, with the head engageable with conventionally available drive systems, such as hexalobe drives. In the preferred embodiment, adequate strength is achieved by selecting the fusing element from a suitable class of metals, such as titanium.

To surgically implant the apparatus 10 as shown in FIG. 2, a dorsalinear incision is made over the hallux 90 extending from the interphalangeal joint 96 to proximally over the metatarsophalangeal joint 97. The hallux 90 is dissected such that both the interphalangeal joint 96 and the metatarsophalangeal joint 97 are clearly exposed. The proximal face 94 of the proximal phalanx 92 and the articular surface of the interphalangeal joint 96 are resected.

A guide wire is driven with a k-wire driver from the interphalangeal joint 96 through the distal end 98 of the hallux 90. The wire is pulled further toward the distal end 98 of the hallux 90 with the k-wire driver until an end of the wire can be positioned at the center of the interphalangeal joint 96. The wire is then driven toward the metatarsophalangeal joint 97 with care taken to position the wire at the center of the proximal face 94 of the proximal phalanx 92. Proper positioning should be confirmed using a fluoroscopy.

Next, a sizer is used to choose the appropriate size of the joint surface element 30. Once the size of the joint surface element 30 has been chosen, the joint surface element 30 is implanted by threading the joint surface element 30 over the guide wire to assure proper placement. Using an impactor and mallet, the joint surface element 30 is positioned so that the upper surface 41 of the joint surface element 30 becomes the proximal face 94 of the proximal phalanx 92 and the stem portion 50 of the joint surface element 30 is closer to the interphalangeal joint 96 than the head portion 40 of the joint surface element 30. The guide wire is then retracted from the distal end 98 of the hallux 90 until the end of the guide wire is even with the upper surface 41 of the joint surface element 30. This should be confirmed using the fluoroscopy.

To implant the elongated fusing element 60 through the interphalangeal joint 96, a cannulated depth gauge is first used to measure the length of the elongated fusing element 60 that is needed. The elongated fusing element 60 must be long enough that the elongated fusing element 60 extends through the interphalangeal joint 96 when it is implanted. A cannulated drill bit may then be used to drill from the distal end 98 of the hallux 90 to the proximal face 94 of the proximal phalanx 92. This will create a channel in the distal phalanx 91 and the proximal phalanx 92 for the elongated fusing element 60 to be implanted in. The elongated fusing element 60 is then driven from the distal end 98 of the hallux 90 using the guide wire until the first end 61 of the elongated fusing element 60 engages the socket 53 of the joint surface element 30. The body portion 63 of the elongated fusing element 60 extends through the interphalangeal joint 96 and the second end 62 rests in the distal phalanx 91. This positioning of the elongated fusing element 60 will fuse the interphalangeal joint 96, such that the distal phalanx 91 and the proximal phalanx 92 are held in linear alignment with one another and no movement can occur within the interphalangeal joint 96.

While the invention has been described in connection with what is presently considered to be the most practical and preferred implementations, it is to be understood that the invention is not to be limited to the disclosed implementations but, on the contrary, is intended to cover various modifications and equivalent arrangements included within the spirit and scope of the appended claims, which scope is to be accorded the broadest interpretation so as to encompass all such modifications and equivalent structures as permitted under the law.

What is claimed is:

1. An apparatus for partial replacement of a metatarsophalangeal joint defined by a proximal face of a phalanx and a distal face of a metatarsal, the apparatus comprising:
    an elongated fusing element configured to restrain movement within an interphalangeal joint and having an end configured for engagement with a socket in a joint surface element; and
    the joint surface element having a head portion and stem portion, the head portion of the joint surface element having a first end with a generally concave surface configured to serve as the proximal face of the phalanx and a second end opposing the first end, the stem portion of the joint surface element having a frusto-conical configuration, a first end attached to the second end of the head portion, and a second end with the socket configured to engage the end of the elongated fusing element, wherein an outer circumference of the first end of the stem portion of the joint surface element is greater than an outer circumference of the second end of the stem portion of the joint surface element,
    wherein the elongated fusing element fuses an interphalangeal joint when the elongated fusing element and the joint surface element are surgically implanted in the metatarsophalangeal joint.

2. The apparatus of claim 1, wherein the socket further comprises an insert for frictionally engaging the elongated fusing element.

3. The apparatus of claim 2, wherein the insert is elastomeric.

4. The apparatus of claim 1, wherein the elongated fusing element is threaded to restrain movement in the interphalangeal joint.

5. The apparatus of claim 1, wherein the elongated fusing element is a compression screw.

6. The apparatus of claim 1, wherein the elongated fusing element is a headless compression screw.

7. The apparatus of claim 1, wherein the head portion and the stem portion are integrally formed.

8. The apparatus of claim 1, wherein an outer circumference of the head portion is greater than the outer circumference of the first end of the stem portion.

9. The apparatus of claim 1, wherein the head portion further comprises:
    a middle region between the first end and the second end, wherein an outer circumference of the middle region is greater than an outer circumference of the first end of the head portion and an outer circumference of the second end of the head portion.

10. The apparatus of claim 1, wherein the generally concave surface is comprised of cobalt chromium.

11. A method of partially replacing a metatarsophalangeal joint defined by a proximal face of a phalanx and a distal face of a metatarsal, the method comprising the steps of:
    surgically exposing the metatarsophalangeal joint and an interphalangeal joint;
    resecting the proximal face of the phalanx;
    implanting a joint surface element in the metatarsophalangeal joint, the joint surface element having a generally concave surface configured to serve as the proximal face of the phalanx and a socket configured to engage an end of an elongated fusing element;
    implanting the elongated fusing element through the interphalangeal joint; and
    engaging the end of the elongated fusing element with the socket of the joint surface element.

12. The method of claim 11, further comprising the step of securing the end of the elongated fusing element with the socket utilizing frictional engagement between the socket and said elongated fusing element.

13. The method of claim 11, wherein the step of surgically exposing the metatarsophalangeal joint and an interphalangeal joint further comprises making a dorsalinear incision.

14. The method of claim 11, further comprising the steps of:
    drilling from an end of the phalanx to the proximal face of the phalanx to create a channel.

15. The method of claim 14, wherein the elongated fusing element is implanted into the channel.

16. The method of claim 11, further comprising the step of:
    using a cannulated depth gauge to determine a length of the elongated fusing element.

17. The method of claim 11, wherein the step of implanting the elongated fusing element through the interphalangeal joint further comprises driving the elongated fusing element from an end of the phalanx to the socket of the joint surface element.

18. The method of claim 11, further comprising the step of:
    using a sizer to determine an appropriate size of the joint surface element.

19. The method of claim 11, further comprising the step of:
    resecting an articular surface of the interphalangeal joint.

* * * * *